US012667477B2

(12) United States Patent     (10) Patent No.:   US 12,667,477 B2

Phillips     (45) Date of Patent:    Jun. 30, 2026

(54) WATERPROOF COVER FOR OSTOMY APPLIANCE

(71) Applicant: Erin Marie Phillips, Cranston, RI (US)

(72) Inventor: Erin Marie Phillips, Cranston, RI (US)

( * ) Notice: Subject to any disclaimer, the term of this patent is extended or adjusted under 35 U.S.C. 154(b) by 341 days.

(21) Appl. No.: 18/205,489

(22) Filed: Jun. 2, 2023

(65) Prior Publication Data

US 2023/0390098 A1     Dec. 7, 2023

Related U.S. Application Data

(60) Provisional application No. 63/348,340, filed on Jun. 2, 2022.

(51) Int. Cl.
*A61F 5/443*       (2006.01)
*A61F 5/449*       (2006.01)

(52) U.S. Cl.
CPC .............. *A61F 5/443* (2013.01); *A61F 5/449* (2013.01)

(58) Field of Classification Search
CPC .......... A61F 5/443; A61F 5/445; A61F 5/448; A61F 5/449; A61F 5/44–58
See application file for complete search history.

(56) References Cited

U.S. PATENT DOCUMENTS

| | | | | |
|---|---|---|---|---|
| 5,785,695 A * | 7/1998 | Sato | ........................ | A61F 5/445 |
| | | | | 604/338 |
| 9,204,990 B1 * | 12/2015 | Berven | .................... | A61F 5/443 |
| 9,750,633 B1 * | 9/2017 | Follenius | ................ | A61F 5/443 |
| 9,757,270 B2 * | 9/2017 | Carrubba | ................ | A61F 5/448 |
| 11,154,415 B2 * | 10/2021 | Johnson | ................ | A61F 5/4404 |
| 2005/0148921 A1 * | 7/2005 | Hsu | ..................... | A61F 13/0209 |
| | | | | 602/48 |

FOREIGN PATENT DOCUMENTS

| | | | | | |
|---|---|---|---|---|---|
| FR | 2396541 A1 * | 2/1979 | ............. | A61F 5/448 |
| WO | WO-0110363 A1 * | 2/2001 | ............. | A61F 5/449 |

* cited by examiner

*Primary Examiner* — Leslie R Deak
*Assistant Examiner* — Linnae E. Raymond
(74) *Attorney, Agent, or Firm* — Feeney IP Law; Daniel W. Sullivan; Alan F. Feeney

(57) ABSTRACT

The present invention provides a waterproof ostomy appliance cover which allows ostomy users to keep their ostomy bag dry when entering wet environments such as, for example, swimming, bathing, and showering. The waterproof ostomy appliance cover creates a waterproof environment for the ostomy bag without the risk of infection and contamination. In addition, this product can also provide for easy and clean disposal of the zip sealed ostomy bag.

4 Claims, 10 Drawing Sheets

WATERPROOF COVER FOR OSTOMY APPLIANCE

CROSS-REFERENCE TO RELATED INVENTIONS

The application claims the benefit of U.S. Provisional Patent Application No. 63/348,340 filed Jun. 2, 2022, the entire disclosure of which is hereby incorporated by reference.

BACKGROUND OF THE INVENTION

Field of the Invention

The present invention relates generally to covers for ostomy appliances. More particularly, the invention provides waterproof covers that allow persons wearing ostomy bags to keep their ostomy bag dry when entering wet environments such as, for example, swimming, bathing, and showering.

Brief Review of the Related Art

A bag is a device specifically made to store internal contents. Typically, a bag comprises a plastic exterior with an opening that can be sealed by irreversible mechanisms such as heat-sealing or sonic welding or reversable mechanisms such as Zip-Lock® mechanisms and closure or clasp devices. When the user seals the bag, it blocks oxygen and moisture from entering the bag which prevents spillage, dampness of internal contents, evaporation of volatile components, and release of foul odors while also reducing the potential for theft of internal contents.

An ostomy is a surgical procedure that creates an opening (stoma) from an organ inside of a human body to outside the body. An ostomy bag is a small pouch used to collect waste from the body. Ostomy bags differ based on where the bags are attached in the intestines such as the colon (colostomy bag), ilium (ileostomy), and urethra (urostomy). Ostomy bags can also differ based on their overall design, for example, there is a one-piece system which fits around the stoma and is attached with a gentle adhesive, a two-piece system comprising a base plate which fits tightly around the stoma, and a bag that attaches to the base plate. In addition, there are closed bags which are best used with firm stools, drainable bags which are best if your stools are very liquid, and mini pouches which are small bags that the patient wears for only a short amount of time. The patient may need to keep the colostomy bag in position against the stoma to receive feces and gas discharged through the stoma. An abdominal belt is usually used to hold the bag in position against the stoma immediately behind the normal beltline of a patient's clothing. In addition, the bag is normally provided with a gas vent to prevent gas build up and over inflation of the bag, and to eliminate offensive odors caused by the escaping gas. It is common practice to provide an exterior deodorizing filter in the gas vent line.

Common reasons that lead to a person requiring a colostomy bag include inflammatory bowel disease, colon cancer, severe acute obstruction, trauma, gunshot wounds and/or other diseases, and injuries and conditions that may require a means for removing bodily waste. Studies have shown that ostomy pouches account for about eighty percent (80%) of global spending on ostomy care. This finding is due to the growing prevalence of ulcerative colitis and inflammatory bowel disease among the aging population. In fact, currently, as many as one million people in the United States live with an ostomy.

Conventional ostomy bags are somewhat waterproof, but must be dried thoroughly, usually with a hair dryer. The barrier, or wafer, however, is not completely waterproof. Upon getting wet, the wafer becomes "gummy" in texture, allowing water to permeate. This can become problematic when ostomy wearers rely on such "waterproofing" without subsequently changing their ostomy appliance. For example, the wafer can lift causing embarrassing leakage of the ostomy bag. Also, water can remain at the attachment site, and this can lead to skin irritations, yeast infection, and other various medical complications that can range in degree of severity. However, to fully change the ostomy appliance (wafer, bag, and various other items that are normally used as well; e.g., paste, barrier rings) can become very expensive. People who have their ostomy supplies covered by insurance are given a limited amount per month.

The device of the present invention will provide a benefit over currently available options, because it protects the entire ostomy appliance, including the wafer. This functionality avoids the concern of moisture build-up and subsequent leaking and skin infections. In addition, this device will keep the ostomy appliance dry, which will prevent the need to replace the ostomy bag as often. This could reduce the excessive global spending dedicated to ostomy care. This device will provide many benefits which can be applied to various industries including the healthcare industry, manufacturing industry, retail industry and combinations thereof.

SUMMARY OF THE INVENTION

This invention is drawn to a waterproof ostomy appliance cover which will allow ostomy users to keep their ostomy bag dry when entering into wet environments. This waterproof ostomy appliance cover provides benefits at the consumer level, because it creates a waterproof environment for the ostomy bag without the risk of infection and contamination. In addition, this product can also provide for easy and clean disposal of the zip sealed ostomy bag. This waterproof ostomy appliance cover provides a benefit in various industries, including but not limited to, the healthcare industry, manufacturing industry, retail industry and combinations thereof.

BRIEF DESCRIPTION OF THE DRAWINGS

The following detailed description of the invention reference is made to the accompanying drawings which form a part hereof, and in which are shown, by way of illustration, specific embodiments in which the invention may be practiced. These embodiments are described in sufficient detail to enable those skilled in the art to practice the invention. Other embodiments may be utilized, and structural and logical changes may be made, without departing from the scope of the present invention.

DETAILED DESCRIPTION OF THE INVENTION

Figure 1:
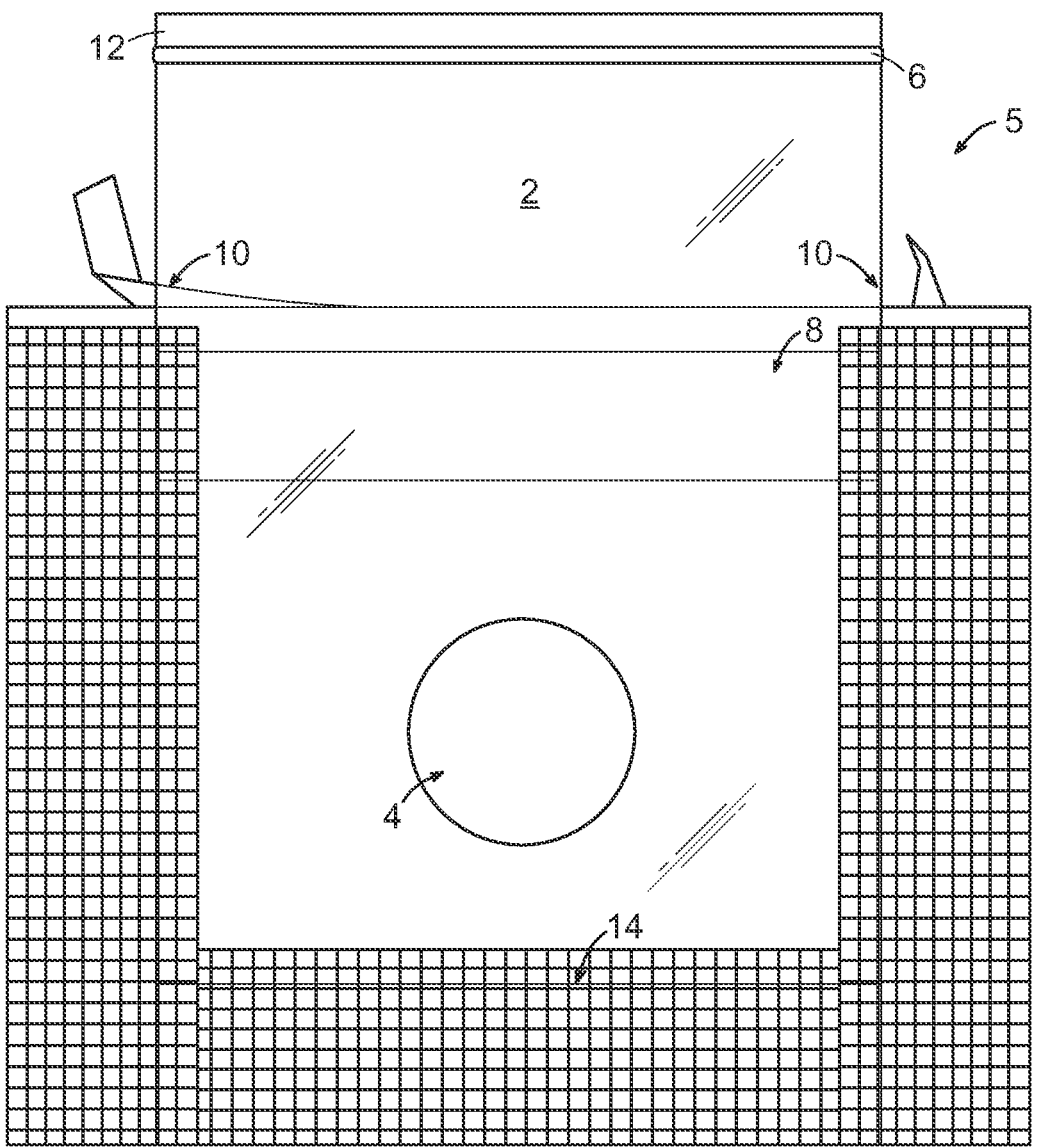
FIG. 1 is a rear view of one embodiment of the ostomy appliance cover of the present invention.

Referring to the Figures, where like reference numerals are used to designate like element, FIG. 1 shows a three-dimensional back side view of the waterproof ostomy appliance cover (5) comprised of an upper region with the ability to be sealed or unsealed (12) (hereinafter referred to as the "mouth"); and two malleable strips comprising opposite side edges with cooperative structures that can be coupled together to interlock (6) (hereinafter referred to as a "zipper"). This embodiment further comprises two external walls, one located on the side proximal to the user's body and the other located on distal to the user's body (hereinafter referred to as proximal external wall and distal external wall). Said proximal external wall and said distal external wall are heat sealed together at the two edges extending vertically up the side of the bag (10) (hereinafter referred to as sides) and at the bottom end (14) (hereinafter referred to as the base). This embodiment is further comprised of an internal space (2) (hereinafter referred to as the compartment) with a hole in the middle lower region of said proximal external wall (4) (hereinafter referred to as the attachment site) and adhesive layers (8) affixed to the two sides, the bottom and the upper portion of said proximal external wall.

Figure 2:
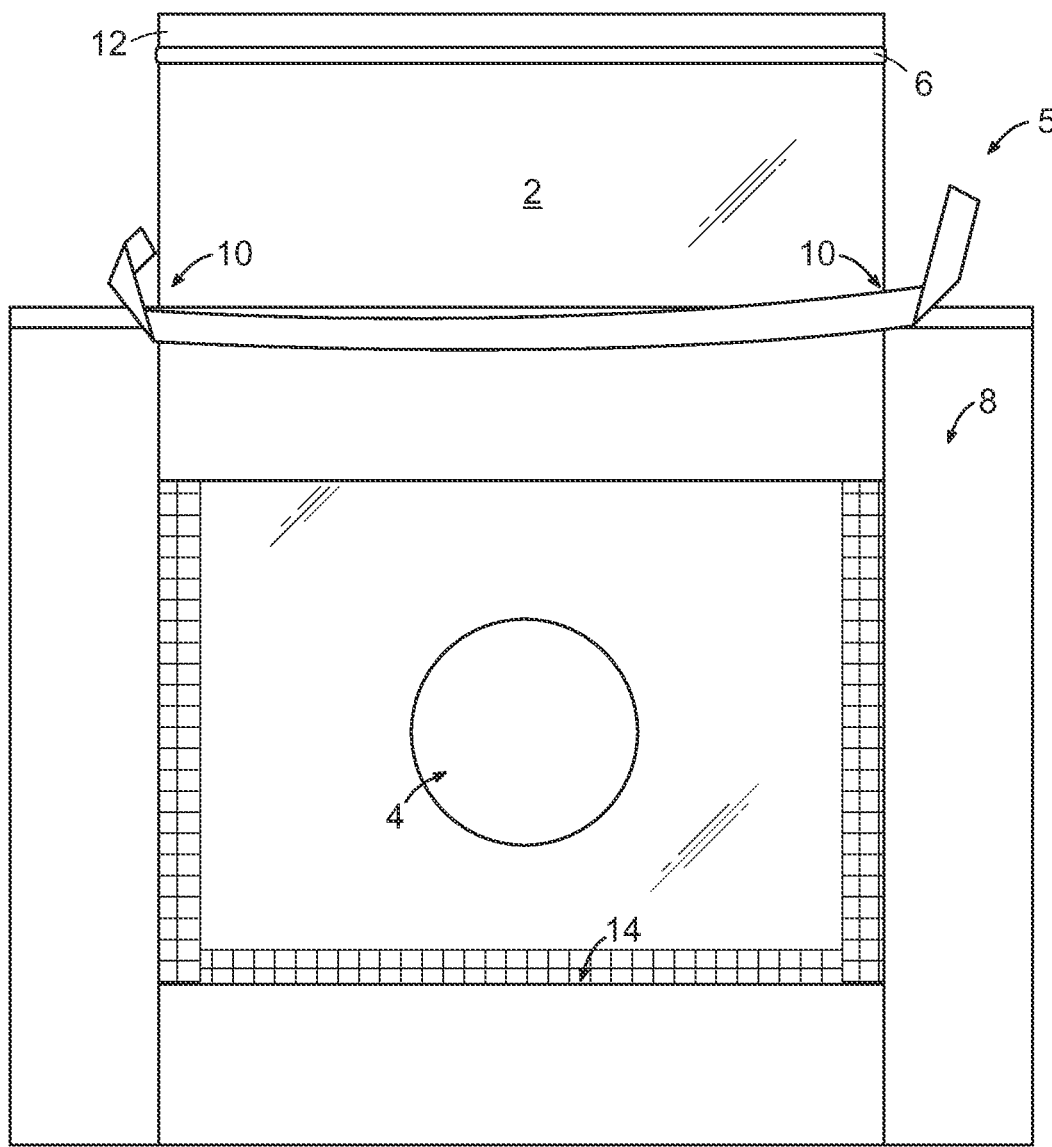
FIG. 2 is a front view of the ostomy appliance cover shown in FIG. 1.

FIG. 2 shows a three-dimensional front side view of the waterproof ostomy appliance cover (5) comprised of a mouth (12), a zipper (6), two sides (10), a base (14), a compartment (2), an attachment site (4), and adhesive layers (8) affixed to the two sides, the bottom and the upper portion of said proximal external wall.

Figure 3:
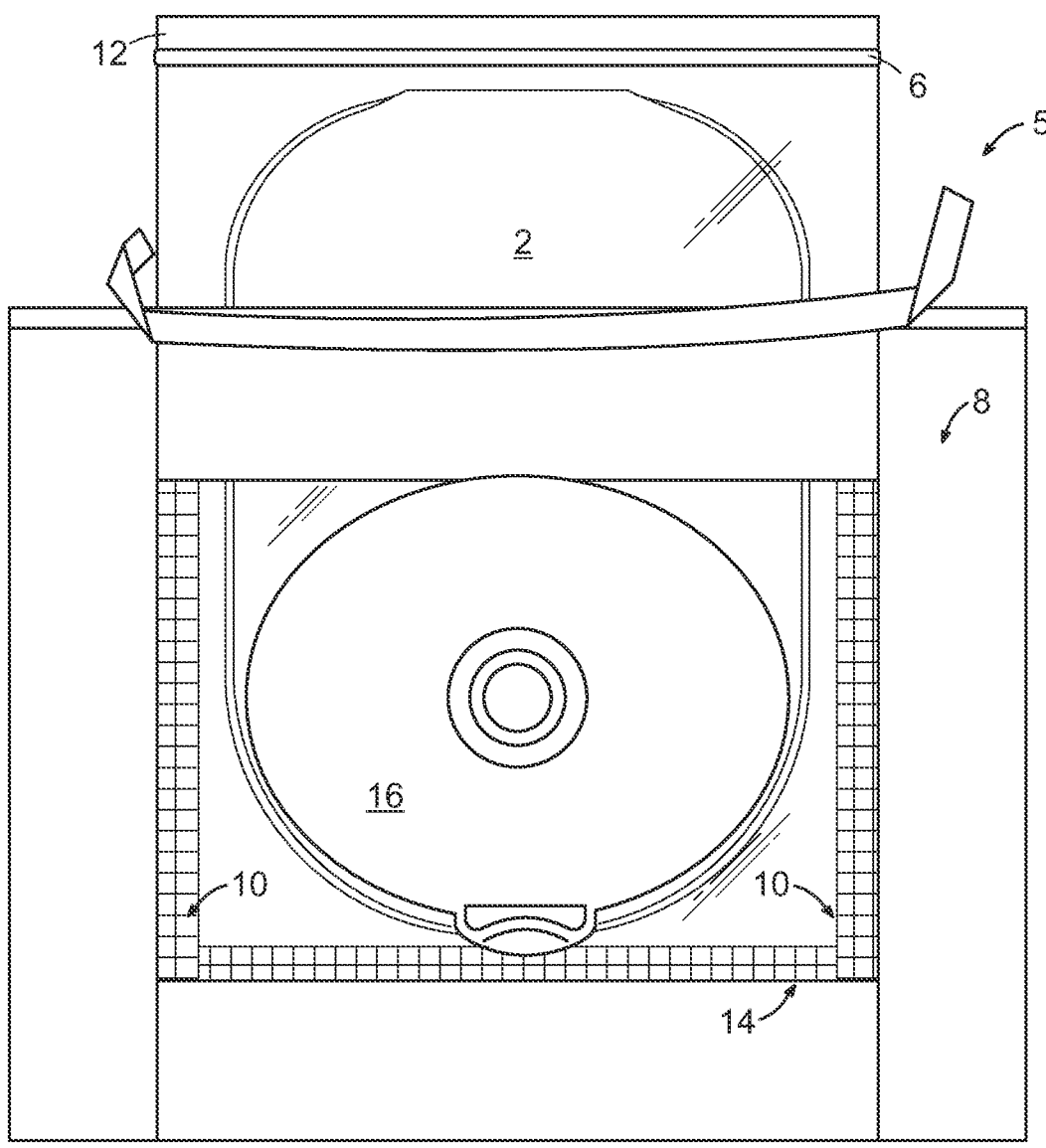
FIG. 3 is a rear view of another embodiment of the ostomy appliance cover of the present invention showing an ostomy bag enclosed within the cover.

FIG. 3 shows a three-dimensional back side view of the waterproof ostomy appliance cover (5) comprised of a mouth (12), a zipper (6), two sides (10), a base (14), and an ostomy bag (16) sealed within said compartment (2). The wafer of the ostomy bag is protruding through the attachment site and into the external environment. The waterproof ostomy appliance cover is also comprised of adhesive layers (8) affixed to the two sides, the bottom and the upper portion of said proximal external wall.

Figure 4:
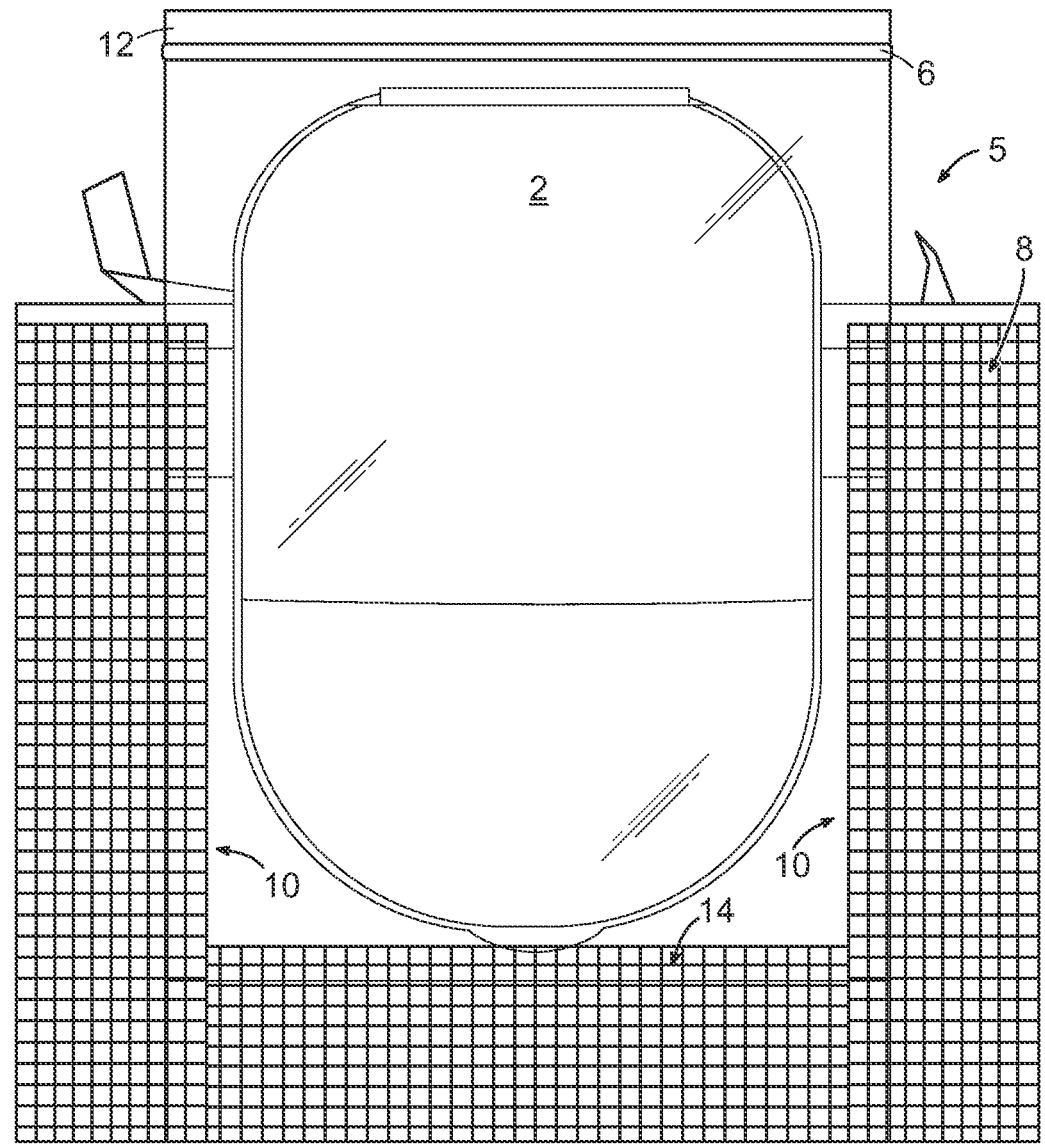
FIG. 4 is a rear view of the ostomy appliance cover as shown in FIG. 2.

FIG. 4 shows a three-dimensional back side view of the waterproof ostomy appliance cover (5) comprised of a mouth (12), a zipper (6), two sides (10), a base (14), and an ostomy bag (16) sealed within said compartment (2), and adhesive layers (8) affixed to the two sides, the bottom and the upper portion of said proximal external wall.

For convenience, certain terms employed in the specification, examples and appended claims are collected here. These definitions should be read in light of the disclosure and understood as by a person of ordinary skill in the art.

As used herein, the terms "comprises." "comprising." "includes." "including." "has" having or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, 'or' refers to an inclusive or and not to an exclusive or. For example, a condition A or B is satisfied by any one of the following: A is true (or present) and B is false (or not present), A is false (or not present) and B is true (or present), and both A and B are true (or present). Also, use of the "a" or "an" are employed to describe elements and components of the invention. This is done merely for convenience and to give a general sense of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, Suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. In the following description, numerous specific details are provided, such as the identification of various system components, to provide an understanding of embodiments of the invention. One skilled in the art will recognize, however, that embodiments of the invention can be practiced without one or more of the specific details, or with other methods, components, materials, etc. In still other instances, well-known structures, materials, or operations are not shown or described in detail to avoid obscuring aspects of various embodiments of the invention Reference throughout this specification to "one embodiment" or "an embodiment' means that a particular feature, structure, or characteristic described in connection with the embodiment is included in at least one embodiment of the present invention. Thus, the appearance of the phrases "in one embodiment' or "in an embodiment in various places throughout this specification are not necessarily all referring to the same embodiment. Furthermore, the particular features, structures, or characteristics may be combined in any Suitable manner in one or more embodiments.

The articles "a" and "an" are used herein to refer to one or to more than one (I.e., to at least one) of the grammatical object of the article. The term "and/or" as used herein is defined as the possibility of having one or the other or both. For example, "A and/or B" provides for the scenarios of having just A or just B or a combination of A and B. If the claim reads A and/or B and/or C, the composition may include A alone, B alone, C alone, A and B but not C, B and C but not A, A and C but not B or all three A, B, and C components.

As an overview, one embodiment the invention is disclosed for a waterproof ostomy appliance cover which provides benefits at the consumer level because it creates a waterproof environment for the ostomy bag without the risk of infection and contamination. In addition, this product can also provide for easy and clean disposal of the zip sealed ostomy bag.

In one preferred embodiment the waterproof ostomy appliance cover can be manufactured through a process of one-shot molding, two-shot molding, or multi-material injection molding and combinations thereof using a manufacturing technique, including but not limited to, ejection molding, 3D printing, injection molding, thermoforming, compression molding, rotational molding, vacuum casting, resin casting, and combinations thereof.

The waterproof ostomy appliance cover can be used to secure and protect an ostomy appliance from the external environment and provides benefits at the consumer level because it creates a waterproof environment for the ostomy bag without the risk of infection and contamination. In addition, this product can also provide for easy and clean disposal of the zip sealed ostomy bag and can be applied to an industry selected from a group consisting of, but not limited to, the healthcare industry, manufacturing industry, the retail industry and combinations thereof.

Mouth

In one preferred embodiment, the waterproof ostomy appliance cover (5) is comprised of an upper end; mouth (12), wherein said mouth comprises of a length equal to the length of said base. In addition, the mouth comprises of one zipper (6) which provides access to one compartment (2).

It should be appreciated that in an alternative embodiment the waterproof ostomy appliance cover can comprise of less than or more than one zipper which can provide access to one or more internal compartments.

It should be appreciated that in an alternative embodiment the mouth can comprise of a length less than or greater than the length of said base. This alternative embodiment may be preferred where the user intends on having a shape that is different than a square or rectangle for instance if the shape of the ostomy bag would be best suited for a waterproof ostomy appliance cover having a shape other than a square or rectangle.

Zipper

In one preferred embodiment the waterproof ostomy appliance cover (5) comprises of one zipper (6) which further comprises of cooperating coupling structures along upper portions of the opposed side panels adjacent said mouth, wherein said cooperating coupling structures comprise of substantially planar outward facing side wall portions; the projecting structures are substantially parallel to one another and to side edges of the bag, the projecting structures extends across the entire width of said bag and the cooperating coupling structures can be interlocked by the pressure of an external force. In addition, the zipper comprises of a mechanism selected from a group consisting, but not limited to, a string zipper, flange zipper, ribbed zipper, double zipper, tamper-proof zipper, slider zipper, particle plow slider, mini slider and combinations thereof.

It should be appreciated that in an alternative embodiment the zipper mechanism comprises of a child resistant assembly. This alternative embodiment may be preferred where the user does not want the waterproof ostomy appliance cover being opened unintentionally by rubbing up against tight clothing or where they do not want back up waterproof ostomy bags covers being opened.

The zipper can be manufactured from a material selected from the group consisting of thermoplastic polymers, polyester, nylon, zinc, brass, aluminum, nickel, nickel-silver alloy, stainless steel and combinations thereof using a manufacturing technique, including but not limited to, extrusion, machining, 3D printing, injection molding, vacuum forming, stamping, forging, casting, die cutting, laser cutting, water jetting, compression molding, powdered metal, hand crafting, molding, sand casting or any other form of additive or subtractive manufacturing or combinations thereof.

Base

In one preferred embodiment, the waterproof ostomy appliance cover (5) is comprised of a lower end; base (14) which further comprises of an irreversible seal between said external walls.

It should be appreciated that in an alternative embodiment, the base can comprise of one or more zippers which can provide access to one or more internal compartments located at said base. This alternative embodiment may be preferred where the user would like to have access to contents from the base of the bag instead of the mouth.

Attachment Site

In one preferred embodiment, the waterproof ostomy appliance cover (5) is comprised of an attachment site (4) located at a centralized region towards the bottom of one of the external walls. The attachment site has a circumference equal to the internal circumference of an ostomy bag wafer.

Sides

In one preferred embodiment, the waterproof ostomy appliance cover (5) is comprised of two external walls which are irreversibly sealed at the vertical ends. The sides are equal in length but have a length greater than the length of said mouth and base.

It should be appreciated that in an alternative embodiment, the sides can comprise of one or more zippers which provide access to one or more internal compartments. This alternative embodiment may be preferred where the user preferred the vertical movement of opening the waterproof ostomy appliance cover as opposed to the horizontal motion that would be required if the zipper was located at the mouth or base.

It should also be appreciated that in an alternative embodiment, the sides can comprise of a length that is less than or greater than the length of said mouth and base. This alternative embodiment may be preferred where the shape of the ostomy bag is best suited for a waterproof ostomy appliance cover having a shape that is not a square or rectangle.

Compartment

In one preferred embodiment, the waterproof ostomy appliance cover (5) comprises of one compartment (2). It should be appreciated that in an alternative embodiment, the waterproof ostomy bag can comprise of more than one compartment. This alternative embodiment may be preferred where the user desires separate spaces to store various items such as an additional pocket to store replacement bags, a replacement wafer or additional items that may or may not be repeated to the ostomy bag itself.

In one preferred embodiment, the compartment is not porous. It should be appreciated that in an alternative embodiment, one or more of said compartments can be comprised of a punctured material; porous.

In an alternative embodiment, the compartment is comprised of an odor management agent distributed in at least one of the compartments to substantially reduce malodor emanating from products disposed within the bag. This alternative embodiment may be preferred where the user would like to mask the odor of the internal contents.

In one preferred embodiment, the compartment can be manufactured from a material with high gas permeability and water vapor transmission rates selected form the group consisting, but not limited to, polyolefins, copolymers of ethylene, substituted olefins, polyesters, polycarbonates (PC), polyamide (PA), acrylonitriles, regenerated cellulose, polylactic acid (PLA) and combinations thereof.

External Walls

In one preferred embodiment, the waterproof ostomy appliance cover (5) comprises of two external walls; one located proximal to the user's body; proximal external wall and the other located distal to the user's body; distal external wall. It should be appreciated that in an alternative embodiment, the bag can comprise of less than or more than two external walls. This alternative embodiment may be preferred where the user desires a waterproof ostomy appliance cover consisting of more than one pocket. In this alternative embodiment, the waterproof ostomy appliance cover could comprise of external walls within the external walls of the waterproof ostomy appliance cover creating various compartments for storage and separating internal contents. In addition, the user may desire an ostomy appliance cover which is not tight to the wafer of the ostomy bag. In this case, a single external wall may be preferred.

In an alternative embodiment, the external walls are comprised of an odor management agent distributed in at least one of the external walls to substantially reduce malodors emanating from products disposed within the bag. This alternative embodiment may be preferred where the user would like to mask the odor of the internal contents.

In one preferred embodiment, the external walls can be manufactured from a malleable material selected form the group consisting of, but not limited to, bioplastics, flame-retardant plastic, polymers, acrylic, butyl, leather, cotton, vinyl, polyurethane, elastomers, silicone, polypropylene and combinations thereof.

In an alternative embodiment, the external walls can be manufactured from a material with high gas permeability and water vapor transmission rates selected form the group consisting of polyolefins, copolymers of ethylene, substituted olefins, polyesters, polycarbonates (PC), polyamide (PA), acrylonitriles, regenerated cellulose, polylactic acid (PLA) and combinations thereof Adhesive Layers In one preferred embodiment, the waterproof ostomy appliance cover (5) is comprised of four adhesive regions (8); one located at each side, one located at the base and one located perpendicular to the mouth but at a region below the mouth. It should be appreciated that more or less adhesive sites can be used based on the user's desires. For example, more adhesives may be preferred where the user would like to secure the mouth of the bag to the user and prevent any potential separation in space between the ostomy bag and the user's body. In this case, the user may desire an additional adhesive located at the region closest to the mouth of the waterproof ostomy appliance cover.

In one preferred embodiment the adhesive region of the adhesive layer can be manufactured from materials selected from group consisting of, but not limited to, silicone, polyurethane, isocyanate, butadiene-styrene, butyl, polyisobutylene, nitrile, epoxy resins, acrylic adhesives, styrene-butadiene rubbers and SIS block copolymers.

In one preferred embodiment the non-adhesive region of the adhesive layer can be manufactured from materials selected from a group consisting of, but not limited to, paper, cloth, felt, foam, polymers, metal foil, polyester, polyimide, films and combinations thereof.

Figure 5:
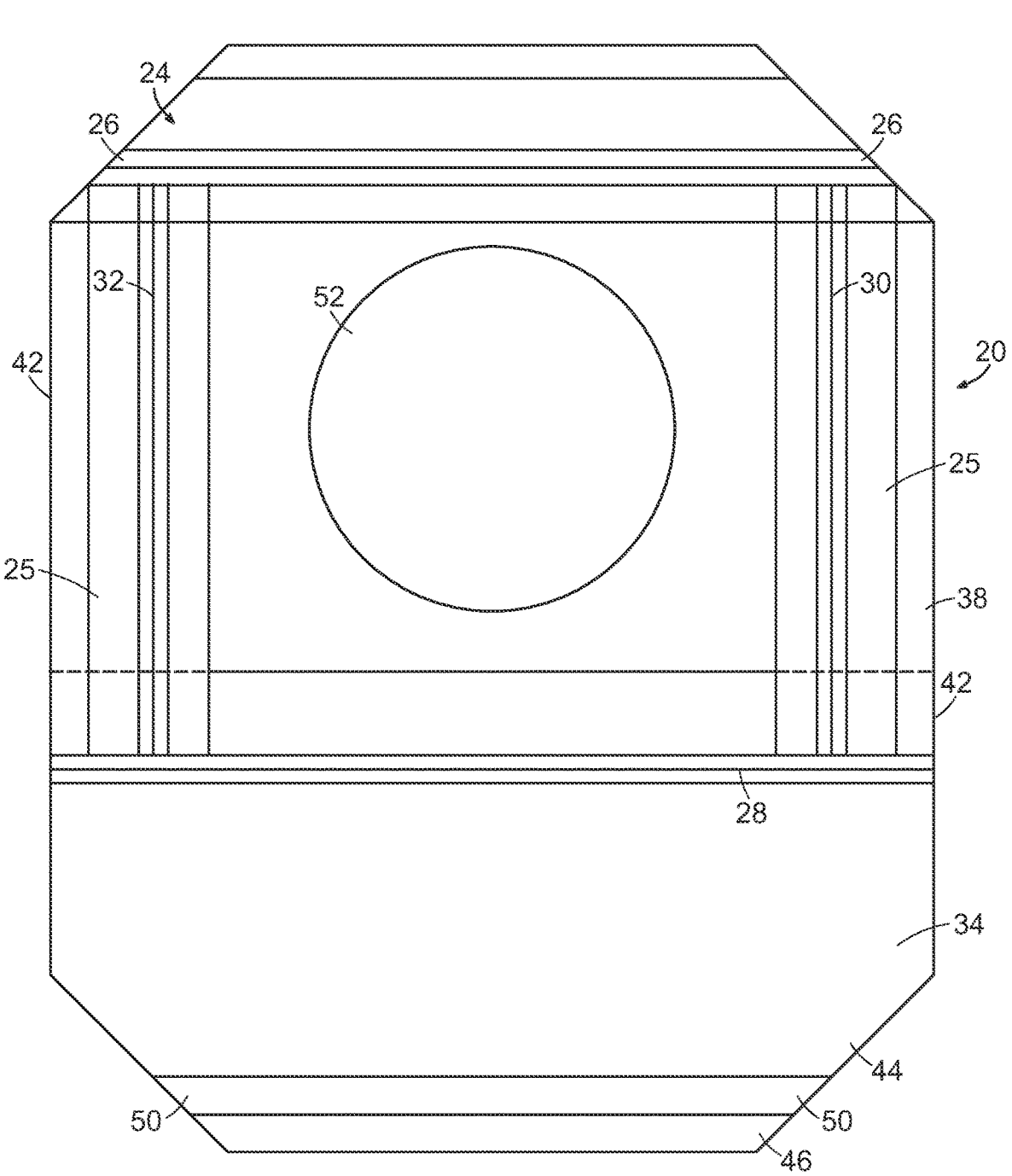
FIG. 5 is a rear view of another embodiment of the ostomy appliance cover of the present invention.

Referring to FIG. 5, in one embodiment, the rear side of the ostomy appliance cover (20), which eventually will be pressed against the body of the person wearing the bag, is shown. The ostomy appliance cover (20) includes a first support frame (24) having an upper member (26), a lower member (28), and opposing first and second sidewall members (30, 32). The upper (26), lower (28), and sidewall members (30, 32) are joined together to define the square-shaped first support frame (24). The upper member (26), lower member (28), and first and second sidewall members (30, 32) can be affixed to the ostomy appliance cover (20) by medical adhesive tape (25) or other suitable fastening means. The upper member (26), lower member (28), and first and second sidewall members (30, 32) can comprise fastening strips that will be pressed against and interlock with complementary fastening strips of a second support frame as discussed further below. The fastening strips are preferably attached by medical adhesive tape that will also be pressed against the body of the wearer.

The ostomy appliance cover (20) comprises a shell (34) having a front panel (36) and rear panel (38) that define an interior compartment (40). The front panel (36) and rear panel (38) have peripheral edges (42). The front (36) and rear panel (38) are fastened together substantially along the entire length of their peripheral edges (42). The shell (38) is split into an upper section (44) and a lower section (46) by a zipper (50) or other suitable fastening means. A traditional zipper (50) may be used in the shell construction (34). The zipper (50) includes first and second sets of complementary zipper teeth for fastening the upper and lower sections (44, 46) together. The upper and lower sections (44, 46) of the bag cover (20) are joined and held together by the zipper (50).

As shown in FIG. 5, the ostomy appliance cover (20) includes a cut-out opening (52) formed in the rear panel (38) of the cover. The square-shaped first support frame (24) surrounds the cut-out opening (52) in the ostomy appliance cover (20). The cut-out opening (52) is aligned with the wafer/barrier appliance (not shown in FIG. 5) when the ostomy bag (not shown in FIG. 5) is held within the ostomy appliance cover (20). That is, the cut-out opening (52) in the ostomy appliance cover (20) is adapted to receive the wafer/barrier appliance.

As discussed further below, the wafer/barrier appliance connects the stoma on the body of the wearer to the ostomy bag. The stoma acts as a passageway so that waste can exit the body. In this way, the interior of the ostomy bag is in fluid communication with the stoma of the wearer of the bag. The ostomy bag can thus collect the removed waste from the stoma.

Figure 6:
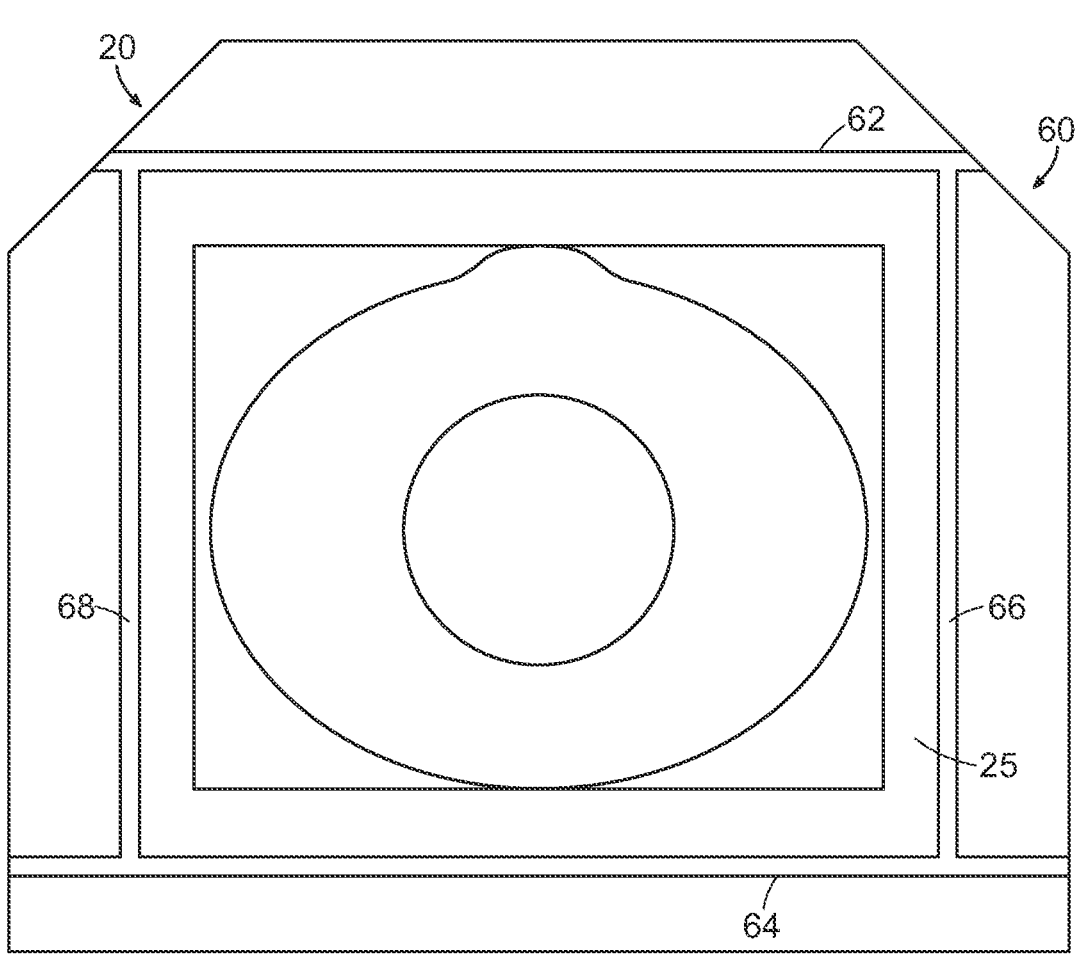
FIG. 6 is a front view of a second support frame for one embodiment of the ostomy appliance cover of the present invention.

Referring to FIG. 6, the front side of a second support frame (60) is shown. The second support frame (60) includes an upper member (62), a lower member (64), and opposing first and second sidewall members (66, 68). The upper (62), lower (64), and sidewall members (66, 68) are joined together to define a square-shaped second support frame (60). The frame surrounds the cut-out opening (52) in the rear panel (38) of the ostomy appliance cover (20). The top portion of the wafer/barrier appliance (70) is visible through the cut-out opening (52). The top portion of the wafer/barrier (70) has an interlocking ring that is secured to a complementary interlocking ring of the bottom portion of the wafer/appliance (71), which is adhered to the body of the wearer as discussed further below.

As shown in FIG. 6, the upper (62), lower (64), and third and fourth sidewall members (66, 68) of the second support frame (60) comprise interlocking fastening strips that interlock with complementary fastening strips of the first support frame (24), which is discussed above. In particular, the upper member (26) of the first support frame (24) can interlock with the complementary upper member (62) of the second support frame (60); the lower member (28) can interlock with the complementary lower member (64), and first and second sidewall members (30, 32) can respectively interlock with the third and fourth sidewall members (66, 68). The interlocking fastening strips of the upper (62), lower (64), and third and fourth sidewall members (66, 68) can be joined together by medical adhesive tape (25) or other suitable fastening means. The fastening strips are preferably attached by medical adhesive tape that will also be pressed against the body of the wearer.

Preferably, the interlocking fastening strips, as discussed above, are pressure-sensitive materials so that the first support frame and second support frame can be releasably attached to each other when they are pressed together. The fastening strips are releasable such that the ostomy appliance cover (20) can be removed from the ostomy bag when needed. The ostomy appliance cover (20) can be reattached to the ostomy bag by pressing the fastening strips so that the cover (20) is affixed to the support frame of the ostomy bag.

Figure 7:
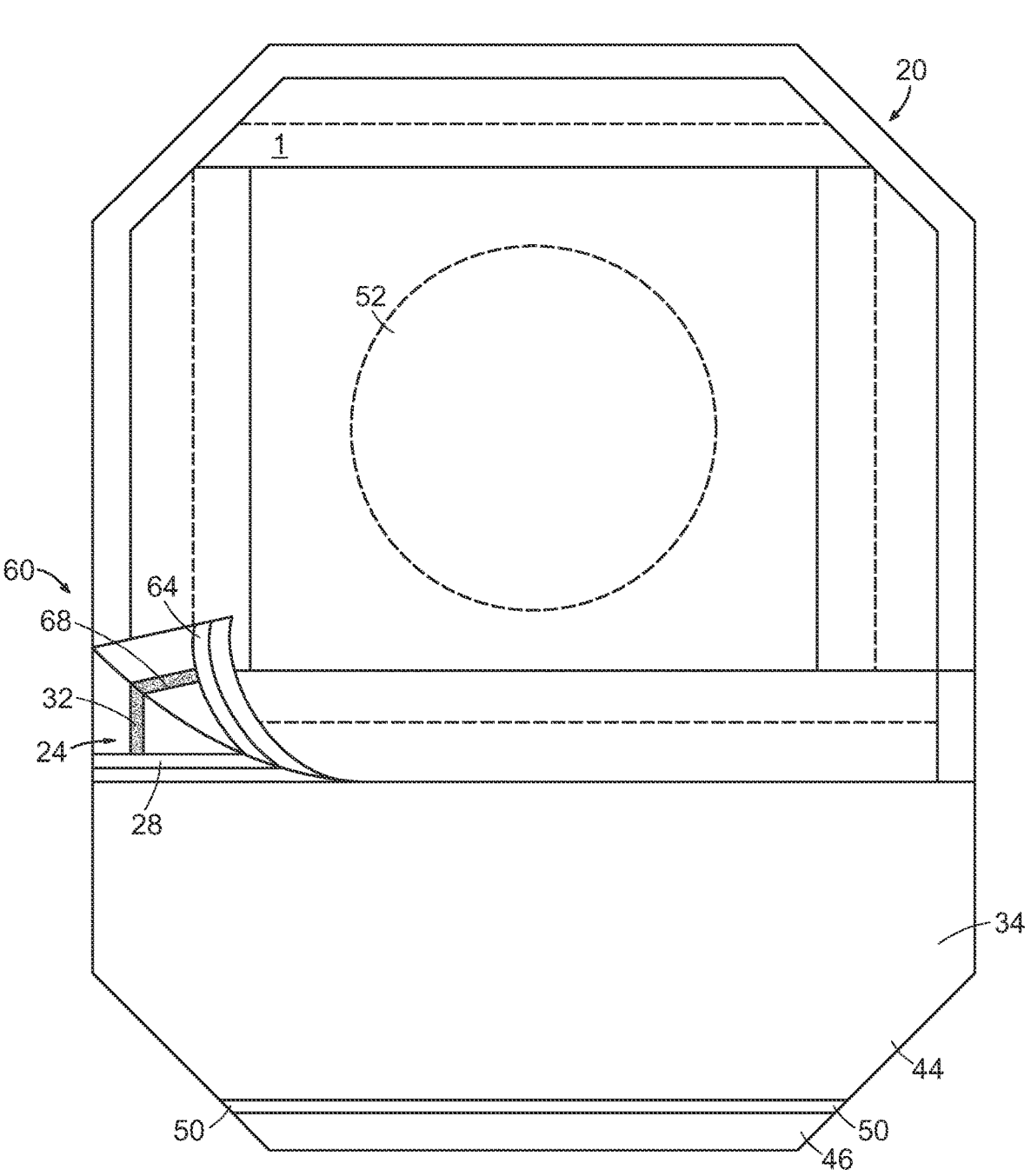
FIG. 7 is a perspective view of the second support frame being pressed and sealed to the first support frame of one embodiment of the ostomy appliance cover of the present invention.

Referring to FIG. 7, the second support frame (60), comprising interlocking fastening strips is shown being pressed and sealed to the complementary fastening strips of the first support frame (24). In particular, the lower member (28) is shown aligning with the complementary lower member (64), and sidewall member (32) is shown aligning with the complementary sidewall member (68). The respective fastening strips are pressed together so that they interlock and form a tight seal.

In another preferred embodiment, the second support frame (60) remains attached to the body of the wearer by adhesive medical tape or other suitable fastening means. In this embodiment, the ostomy appliance cover (20) can be releasably attached to the second support frame (60) by pressing the fastening strips together. The fastening strips of the first support frame (24) interlock with the complementary fastening strips of the second support frame (60). In a subsequent step, the ostomy appliance cover (20) can be removed from the second support frame (60) by pulling upwardly on the tabs (72). The first support frame (24) is detached from the second support frame (60) by grasping the frame and pulling upwardly. In this way, the first support frame (24) is separated from the second support frame (60).

As discussed above, in a preferred embodiment, interlocking fastening strips are preferably used for releasably attaching the ostomy appliance cover to the ostomy bag. Interlocking fastening strips are described, for example, in U.S. Pat. Nos. 4,829,641 and 4,907,321, the disclosures of which are hereby incorporated by reference. Such fasteners are used, for example, in Ziploc® plastic bags. Other suitable fastening means also can be used in accordance with the present invention. For example, the ostomy appliance cover and ostomy bag may be joined by tiny hook and loop fabric fasteners, commonly referred to as Velcro™. In another embodiment, the ostomy appliance cover and ostomy bag can have complementary male and female members that interlock with each other. These complementary interlocking members can be joined with each other to form an assembly. Other suitable fasteners include, for example, tie-down clips, clasps, snap connectors, snap buttons, laces, ties, loops, button/button holes, hook and loop fastener fabric, and combinations thereof.

Figure 8:
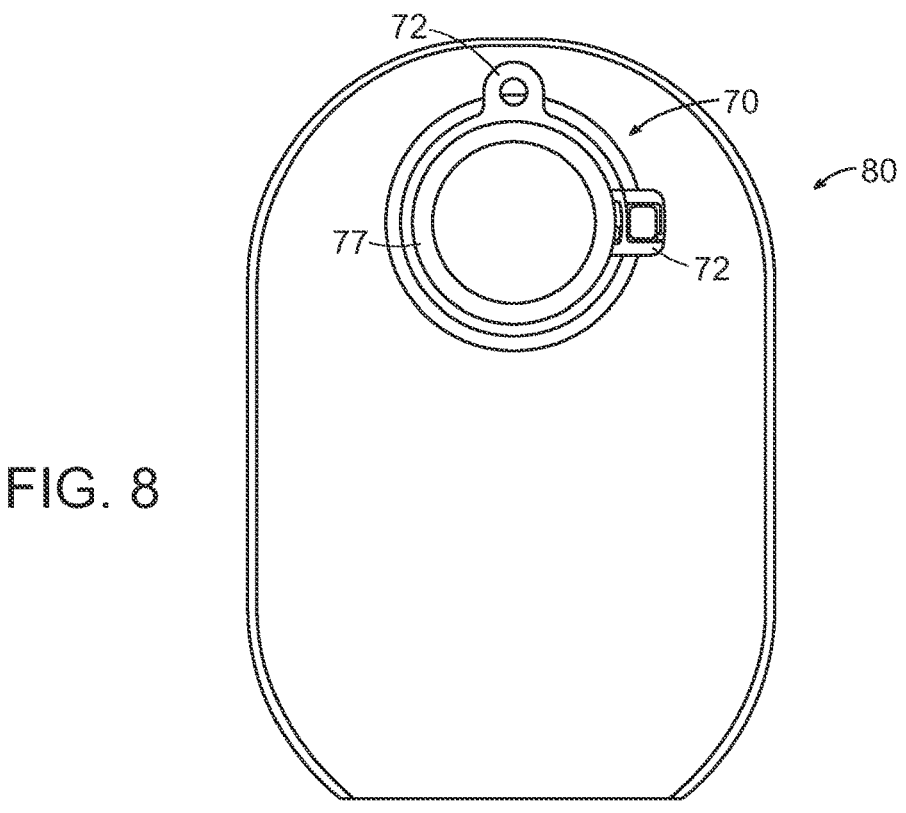
FIG. 8 is a rear view of one embodiment of an ostomy bag for use in accordance with the present invention.
Figure 9:
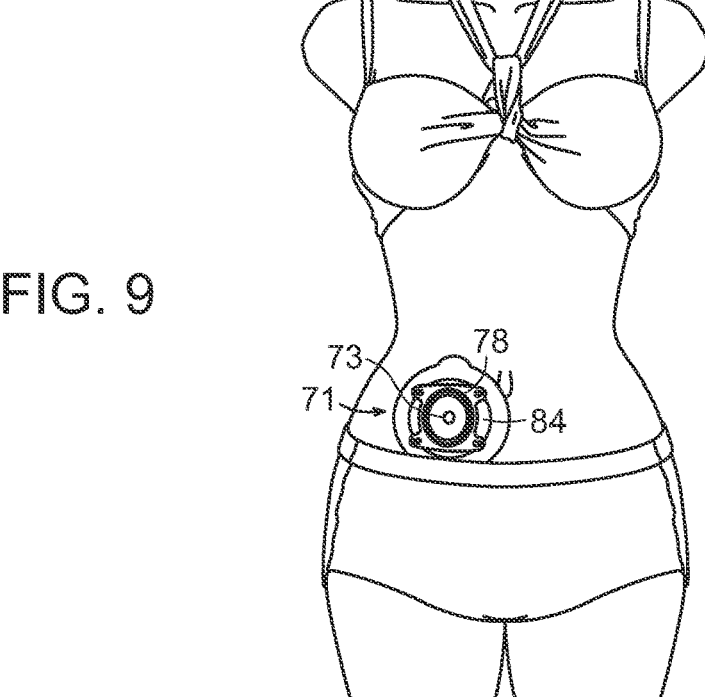
FIG. 9 is a front view of a person wearing one embodiment of a two-piece wafer appliance of the present invention, wherein the bottom portion of the wafer appliance is visible.
Figures 9A, 10:
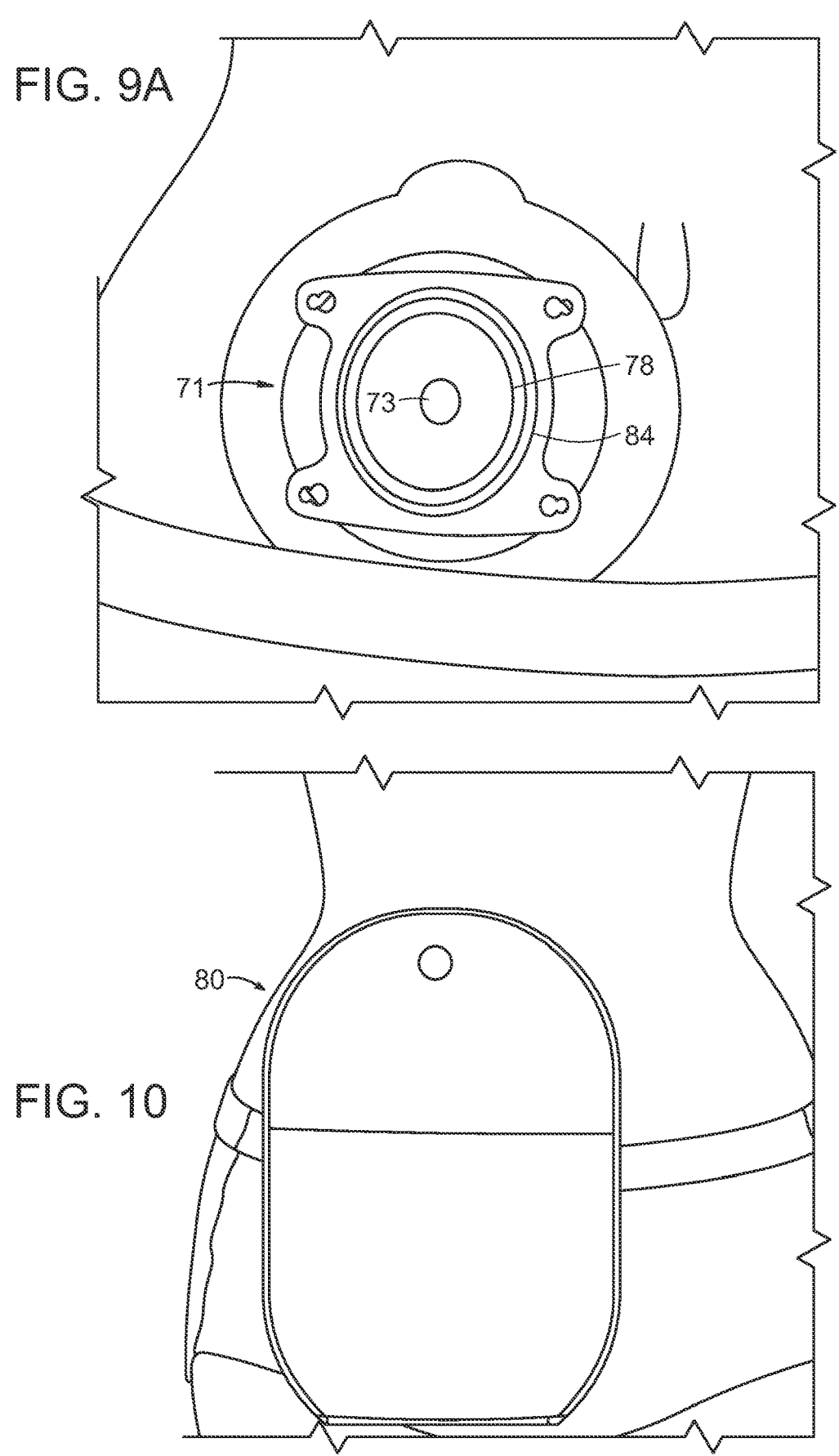
FIG. 9A is a close-up view of the bottom portion of the wafer appliance as shown in FIG. 9.
FIG. 10 is a front view of one embodiment of an ostomy bag for use in accordance with the present invention.

Referring to FIG. 8, a conventional ostomy bag (80) that can be used in accordance with the present invention is shown. In FIG. 8, the wafer/barrier is a two-piece appliance, and the top portion of the wafer/barrier (70) is visible through the opening (82) in the ostomy bag (80). The top portion of the wafer/barrier (70) has a generally flexible interlocking ring (77) that is secured to a complementary interlocking ring (78) of the bottom portion of the wafer/appliance (71). The top portion of the wafer/barrier (70) also includes an outwardly extending tabs (72). The stoma for the person wearing the In practice, the interlocking ring (77) is snap-fitted onto the interlocking ring (78). Referring to FIGS. 9 and 9A, the bottom portion of the wafer/appliance (71) is shown. The bottom portion includes a base plate (84) having the interlocking ring (78). The base plate (84) is affixed to the body of the wearer by an adhesive pad; and the stoma is generally indicated at (73).

Figures 11, 12:
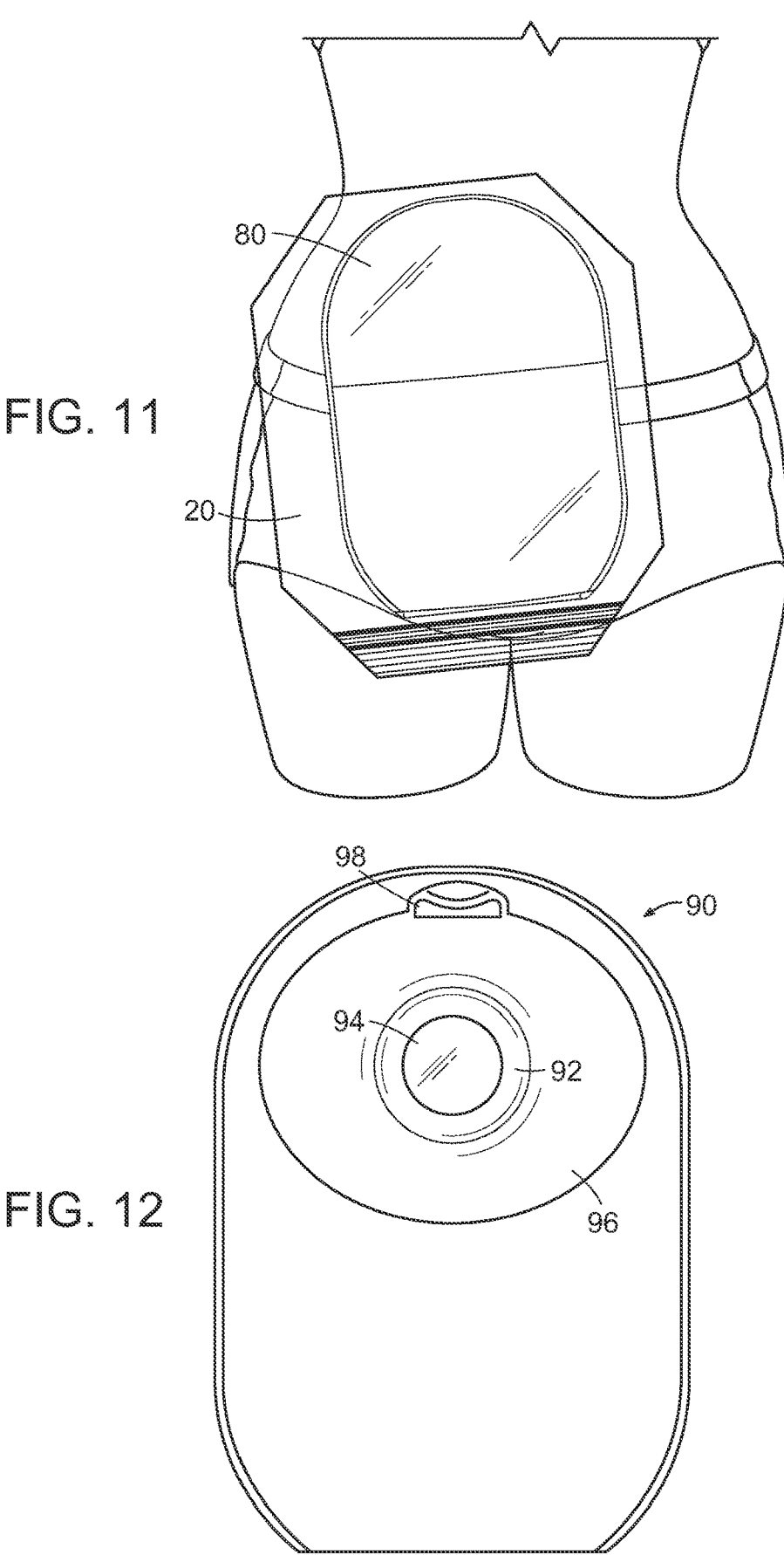
FIG. 11 is a front view of one embodiment of an ostomy appliance cover of the present invention showing the appliance cover enclosing the ostomy bag and being affixed to the body of a wearer.
FIG. 12 is a rear view of one embodiment of a one-piece wafer appliance of the present invention.

In FIG. 10, the ostomy bag (80) is shown secured to the body of the wearer. As described above, the ostomy bag is locked in place by the top portion (70) of the wafer/appliance snap-fitting onto the bottom portion (71) of the wafer/appliance. In FIG. 11, one embodiment of the ostomy appliance cover (20) of the invention is shown enclosing the ostomy bag (80) and affixed to the body of the wearer.

In FIG. 12, a one-piece wafer/appliance (90) is shown. The one-piece wafer/appliance (90) includes an adhesive seal (92) around the opening (94) for the stoma and an adhesive ring (96) and outwardly extending tab (98). The one-piece wafer/appliance (90) can be used in accordance with the present invention.

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressed quantities of ingredients, reaction conditions, and so forth use in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

The above discussion is meant to be illustrative of the principle and various embodiments of the present invention. Numerous variations, combinations and modifications will become apparent to those skilled in the art once the above disclosure is fully appreciated. It is intended that the following claims be interpreted to embrace all such variations and modifications.

I claim:

1. An ostomy appliance cover assembly, comprising a shell having a front panel and a rear panel, the panels being joined together to define an interior compartment, the rear panel having a circular cut-out opening;

a first support frame attached to the shell and surrounding the cut-out opening, the first support frame being square-shaped and comprising a first upper fastening member, a first lower fastening member, and first and second side fastening members;

a second support frame, the second support frame being removably attached to the first support frame, the second support frame being square-shaped and comprising a second upper fastening member, a second lower fastening member, and third and fourth side fastening members, wherein the second upper fastening member, second lower fastening member, and third and fourth side fastening members are joined together by adhesive tape and configured to be attached to a wearer of the ostomy appliance cover assembly by the adhesive tape, wherein the first upper fastening member, first lower fastening member, first and second side fastening members of the first support frame, and the second upper fastening member, second lower fastening member, and third and fourth side fastening members of the second support frame are complementary interlocking fastening strips that interlock with each other so that the second support frame is removably attached to the first support frame; and an ostomy bag having a wafer appliance, the ostomy bag being enclosed in the shell so that the wafer appliance extends from the circular cut-out opening.

2. The ostomy appliance cover assembly of claim 1, wherein the shell has an upper section and a lower section, the sections being fastened together by a zipper.

3. The ostomy appliance cover assembly of claim 1, wherein the wafer is a two-piece sub-assembly having a top portion and a bottom portion, the top portion extending from the circular cut-out opening; and the bottom portion being configured to be affixed to a wearer of the ostomy appliance cover assembly so that the top and bottom portions are joined together.

4. The ostomy appliance cover assembly of claim 1, wherein the wafer appliance is a one-piece device having an adhesive ring for adhering the wafer to a wearer of the ostomy appliance cover.

\* \* \* \* \*